United States Patent [19]

Poveromo

[11] Patent Number: 4,797,099
[45] Date of Patent: Jan. 10, 1989

[54] RESILIENT DENTURE CONNECTING DEVICE

[76] Inventor: Melvin D. Poveromo, 14135 N. Miami Ave., Miami, Fla. 33168

[21] Appl. No.: 156,120

[22] Filed: Feb. 16, 1988

[51] Int. Cl.$^4$ .............................................. A61C 13/22
[52] U.S. Cl. ..................................................... 433/169
[58] Field of Search ........................ 433/168, 169, 180

[56] References Cited

U.S. PATENT DOCUMENTS 4,205,442  6/1980  Zahn ..................................... 433/170
4,579,528  4/1986  Staubli ................................. 433/169

Primary Examiner—Robert Peshock
Attorney, Agent, or Firm—John Cyril Malloy

[57] ABSTRACT

A resilient denture connecting device for utilization with a male/female attachment means to an abutment tooth, which includes a distally extending shank and a housing sized and configured to nest over the shank and pivot means pivotally interconnecting the shank and housing for swinging movement of the housing relative to the shank and said pin dwelling in a slot which permits of vertical movement of adjustment through a predetermined limited range of movement and the device further includes a biasing means normally urging the housing in a normal untilted position but yieldable vertically and swingably so that the housing is adapted to move vertically and in a distal hinge direction in response to masticating loads and to be reboundingly restored to a normal position by the resilient means.

12 Claims, 2 Drawing Sheets

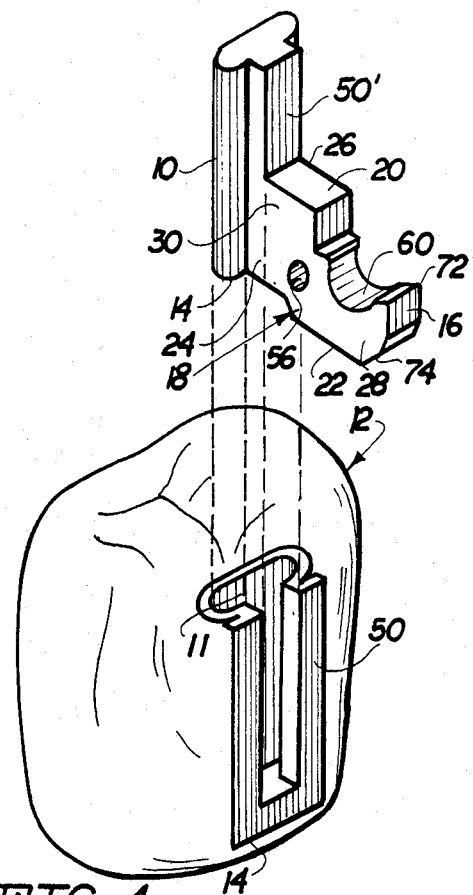
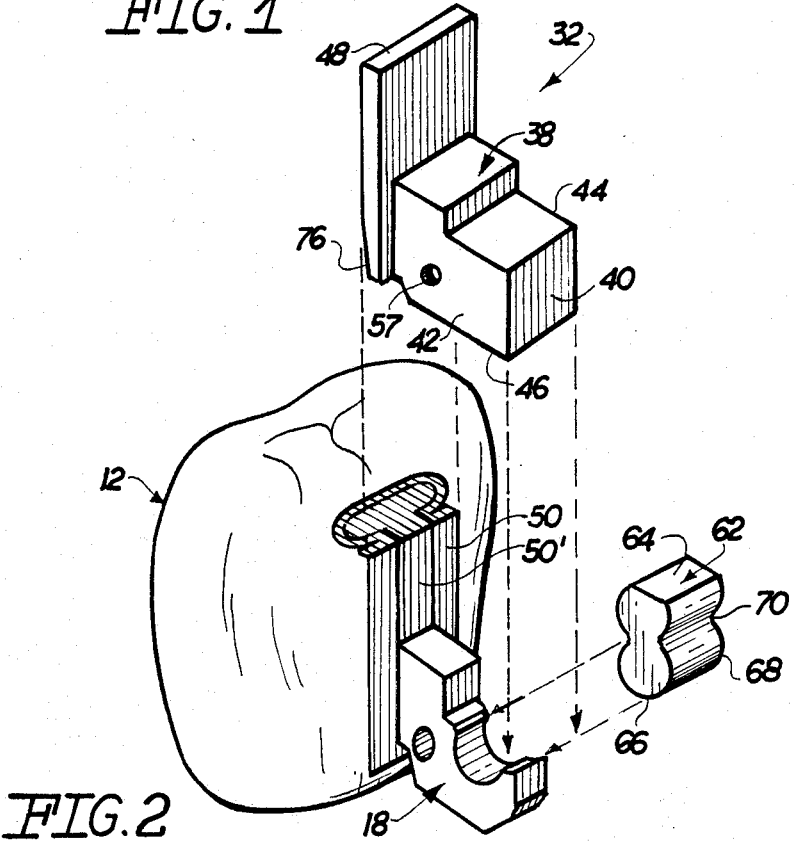
FIG. 1
FIG. 2

RESILIENT DENTURE CONNECTING DEVICE

FIELD OF THE INVENTION

This invention relates to a resilient denture connecting device. More specifically, this invention relates to the general field of connector devices that "link" the crown of the abutment tooth and the partial denture that is fabricated to attach thereto—and, more specifically, the invention pertains to a resilient type of connector which allows the partial denture to settle during masticating loads—and immediately "rebound" to the original position of fabrication, which s in a passive state resting upon the gingival tissue.

STATEMENT OF THE PRIOR ART

There are primarily two types of dental connector devices:

(1) RIGID CONNECTOR DEVICES

These consist of various dental connectors which connect the crown of the abutment tooth to the partial denture.

The design of the rigid connectors is such that the "link" is affixed firmly between the crown and the partial denture.

The principle is "to prevent the partial denture from settling onto the tissue and bone beneath the partial denture." Studies have shown that these undue forces can create adverse effects upon the edentulous ridge—therefore—the design of rigid systems.

(2) RESILIENT CONNECTOR DEVICES

These consist of various dental connectors which connect the crown of the abutment tooth to the partial denture.

The design of the resilient connectors is such that the "link" is fixed between the crown and the partial denture but the mechanics of the various designs allow vertical settlement of the partial denture—to a degree, usually established by the manufacturer, of approximately 0.4 mm. to 0.6 mm.

The principle is "to allow the partial denture to settle vertically during masticating loads (to a point from 0.4 mm. to 0.6 mm.

The intention is to reduce the vertical stress or force imposed upon the crown of the abutment tooth that is supporting this connector as masticating loads are imposed upon the partial denture.

As an example, if the height of the crown of the abutment tooth is identical to the height of the first tooth (or teeth) on the removable partial denture, and a masticating load is imposed upon this removable partial denture, the intention is to allow the partial denture to settle (to a point of 0.4 mm. to 0.6 mm.) with no imposition or force imposed upon the crown of the abutment tooth.

The conventional resilient connectors contain "spacers" that are used in the fabrication of the partial denture, which when removed prior to insertion of the partial denture, will allow this vertical settlement. (The spacers are from 0.4 mm. to 0.6 mm. in thickness.)

DISADVANTAGES OF PRIOR ART

Since there is "no standard" thickness of the mucosal tissue in the edentulous ridges, there can be no uniformity in standard connector devices which "attempt" to utilize the mucosal tissue as a method of "rebounding" the partial denture to the original upright position.

Because of the fact that most removable partial dentures begin in the cuspid and first and second bicuspid area, the masticating loads are usually distal to the fixed crown of the abutment tooth.

The resultant forces are usually a hinge type. Using the crown of the abutment tooth as a "fulcrum" the trajectory is such that the distal portion of the partial denture will settle primarily at the end of the partial denture, with a gradual elevation of this horizontal plane to the denture connector itself.

It is therefore obvious that the thickness of the mucosa on the edentulous ridge is not being utilized in an even manner to affect even displacement of this tissue with the capability of utilizing the physiological properties of this mucosa to "rebound" the partial denture of its original position.

Physiological Consideration of Mucosal Tissue On Edentulous Ridges

"A removable partial denture base that rests on edentulous ridge tissue and expects the tissues to support the occlusal load is utilizing tissue as it is not used anywhere else in the body." "The success of a base then is dependent on how the tissues are handled and how the forces are transmitted." This is quoted from Joseph A. Clayton, D.D.S. M.S., professor of Dentistry, Crown and Bridge Department, University of Michigan School of Dentistry. (Dental Clinics of North America-Vol. 24.)

With the use of removable partial dentures, some bone resorption will always occur, however, the are variables that can control the rate of bone resorption.

When the mucosal tissue is depressed by any means, it will become displaced. This displacement is considered normal—providing the displacement is not allowed to remain continuous. In this event, the tissue becomes deformed, and because of the physiological activities (loss of cell fluid, and oxygen) this deformation tends to increase the rate of bone resorption.

Studies have shown that "intermittent" displacement creates a healthy environment to the mucosal tissue and stimulates the tissue.

"The tissue effect could be intermittent if the base (partial denture) is free to move away from the bone with the rebounding tissue. It is important then, when function ceases, that tissue fluids be permitted to return. In comparison, tissue held in a deformed state with vessels occluded may lack oxygen and nutrients, which could result in cell damage and continuous tissue pressure on the underlying bone-factors that modify the rate of bone resorption." This is quoted from Joseph A. Clayton, D.D.S. M.S., Professor of Dentistry, Crown and Bridge Department, University of Michigan School of Dentistry. (Dental Clinics of North America-Vol. 24.)

SUMMARY OF THE INVENTION

The present invention is directed to the provision of a connector device that is the intermediate link between any precision or semi-precision attachment that is incorporated within the crown of the abutment tooth and the removable partial denture.

This connector device is designed to allow a resilient action such that the removable partial denture may settle under masticating loads, and rebound this partial denture to its original upright position. In this manner, there is no continuous deformation of the mucosa of the edentulous ridge.

Generally, the connector device contains a housing 32 which fits over any extension shank 18 on any denture attachment.

The housing 32 (which is eventually incorporated within the partial denture) along with he partial denture can accommodate the masticating loads in the direction of (a) distal hinge motion, (b) vertical motion, (c) the combination of distal hinge and vertical in any possible direction or angle that is assumed by the masticating load forces, and (d) lateral rotational movement.

The housing 32 contains a fulcrum pin 58 in a vertical slot or recess 56 which allows the housing to hinge as well as settle in a vertical direction.

Within the housing 32 is a "Figure 8" rubber cylinder 62, which rests upon the male shank area. On top of the shank 18 under masticating loads the rubber cylinder will deform and compress vertically, distally, or a combination of both.

The male shank has concave recesses 60 on either side of the rubber cylinder 62 to allow the "bulk" of compression of the rubber cylinder as masticating loads are imposed upon the housing, as well as to retain the rubber cylinder from dislodgement under distal forces. The concavity 60 accommodates the lower portion of the rubber FIG. 8 cylinder. On either side of this concavity, and slightly above the concavity 60 there exists small concavities including a greater arc 61 and a lesser arc 61'.

Distal to the rubber cylinder, the concave area is of a wider arc 61, since the tendency under masticating loads is to force this rubber cylinder distally as well as vertically.

This distal concavity along with the resiliency of the rubber cylinder forces a "rebounding effect" upwards to the top of the housing.

The tension of the rubber cylinder 62 as well as the vertical upright of the face plate 48 (flat rectangular plate), combined with the fulcrum pin 58 forces the housing 32 to return to its original fabricated position as the energy of compression stored in the rubber cylinder 62 is released.

There is a recess of approximately 0.4 to 0.6 mm. under the mesial portion of the housing which s the allowance space for normal displacement of the mucosal tissue. This term "normal" is used as the "average" mucosal displacement standard.

The rubber cylinder 62 will allow hinging to an angle where a portion of the housing will contact the male shank at the distal occlusal point. This hinging is beyond normal requirement, however, in the event of abuse of the case, it is a protection point to limit swinging movement of the housing.

On the gingival portion of the face plate 48 there is an angle cut 76 which allows hinging effect to clear the existing attachment that is within the crown of the abutment tooth. In addition, there is at the distal, gingival portion of the male shank an additional angle 74 which will allow the housing to hinge since the housing is enclosing the male shank.

The design of the FIG. 8 rubber cylinder 62 may assume several different forms and shapes. It may be rectangular in shape. It may be a complete circle in design. It may be a combination of a variety of "arcs'- 'and square forms. The intention is to effect the optimum design of this rebounding rubber to accomplish the resilient effect of the connector and with the mechanics of returning the housing (and removable partial denture) to the original upright fabricated position, thereby removing the continuous load or force that is otherwise imposed upon the mucosal tissue.

In order to replace the rubber cylinder 62 in the event of fatigue, the fulcrum pin is removed and the male shank 18 is withdrawn. At this point, the rubber cylinder 62 is replaced. The male shank 18 is then reinserted and the fulcrum pin 58 inserted. The fulcrum pin 58 is located on the lingual side of the partial denture and covered with the normal resin used in processing of the denture. This area of resin is removed, and restored after replacement of the rubber cylinder.

Application of the Invention

The present invention may be used with a variety of existing manufactured precision and semi-precision attachments. Slight modification can be made with any system to incorporate the invention as an additional connector to allow the resilient, "rebound" principle as set forth above.

Since they are too numerous to describe, the design shown is a type that is integral with the male portion of the male/female attachment means of the shank and abutment tooth 12. In a modification, not shown, suitable connector means, such as a screw fastener may be utilized to connect the shank 18 to the male/female attachment means of the device to the abutment tooth. The dimensions of the invention are such that it will accommodate the bulk area necessary for these expansion screws, as well as those attachments that do not contain similar expansion devices.

Modification

An additional method of accomplishing this rebound effect is by utilizing a vertical coiled spring in the identical area of the rubber cylinder shown in the drawings.

Prior Art contains applications of "a vertical spring" however, the position of the spring, which is usually directly above the fulcrum ball on a few attachments does not provide the effect of resisting a distal hinge load as does the spring located distally and on an even horizontal plane as the fulcrum pin.

One can relate, as an example, a simple "see saw" which consists of a horizontal board balanced in the center by a fulcrum (pipe).

At rest, in theory, the horizontal board remains balanced an parallel to the ground.

When a weight is placed on one end, the end will depress, and when the weight is removed, there is no active action that will enable the end of the board to upright itself to the original horizontal position.

If, a spring, or rubber cylinder is placed immediately to the right of the fulcrum, and contacts the horizontal board from beneath, then this will maintain the horizontal balance of the board and the board will remain parallel to the ground.

When a weight is placed on the right end, as an example, the board will depress, and when the weight is removed, the action of the rubbery cylinder and/or the coiled spring will force the board to its original position, actively, thereby resulting as a force opposing the distal hinge load or force.

With prior art, the coiled spring is placed above the fulcrum point, and relating to the example above, this tends to reverse vertical loads primarily with no active affect on the hinging or distal loads which occur primarily with removable partial dentures.

The positioning of the rebounding mechanism is influential in the active rebounding effect of a hinge load, and in this disclosure the position of the rebounding cylinder, or coiled spring, is in the optimum position for rebounding effects of a hinge action that is spaced distally of the fulcrum pin. The coiled spring resists vertical load primarily, but with no direct active effect to resist hinging action. The initial tendency for a removable partial denture is to hinge because of its position in relation to the edentulous area.

BRIEF DESCRIPTION OF THE DRAWINGS

FIG. 1 is an exploded perspective view of an abutment tooth and the shank of the connecting device;

FIG. 2 is an exploded perspective view of the shank applied to an abutment tooth and the housing and biasing means of the connecting device;

DESCRIPTION OF THE PREFERRED EMBODIMENT

Figure 3:
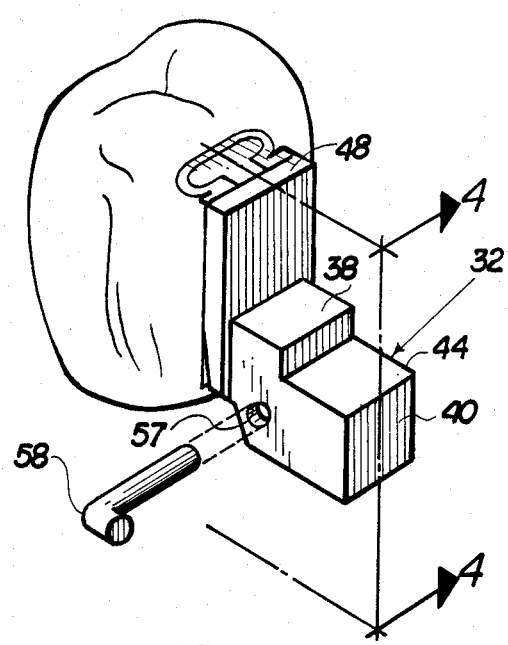
FIG. 3 is a perspective view of the abutment tooth and connecting device.
Figure 4:
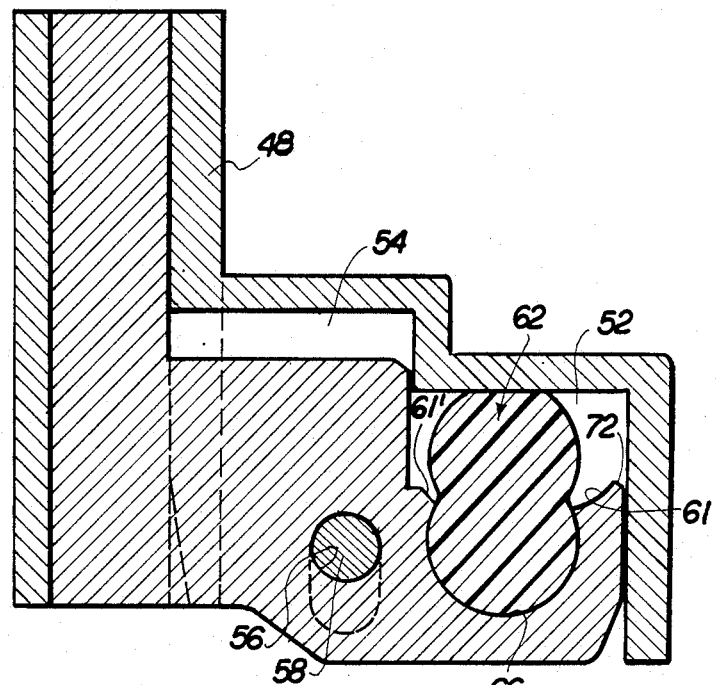
FIG. 4 is a view in cross-section taken on the plane 4—4 of FIG. 3 and looking in the direction of the arrows.

Referring to the drawings, there is shown the resilient denture connecting device. It has a proximal end and a distal end, the distal end being rearwardly in the mouth. A male/female attachment means is provided to connect the device to the abutment tooth 12, as is conventional in the art. The attachment means in the abutment tooth may be considered to have a surface facing the gingival tissue 14 and a distally facing abutment surface 50. The attachment means includes a distally extending rigid shank 18, in this case shown integral with the male portion 10 which is slidingly and securely received in the female portion 11 of the attachment means. As shown, the shank 18 has an upper surface 20 and a lower surface 22. It, also, has a distal surface 16 and a pair of side surfaces 24 and 26. Its upper surface is stepped so that there is provided a distal portion 28 of a lesser height than the intermediate portion 30.

Referring now to the housing 32, it has an open bottom 46 which defines a mouth and it is configured, as explained more fully hereinafter, so as to be nested over the shank in assembly. As shown, the housing 32 has a roof 38 with an upper surface, which, as shown, is stepped, a distal wall 40 with a distal surface, and a pair of opposing side walls 42 and 44. The housing is sized to receive the shank with the side walls of the housing 42, 44 confronting the side surfaces 24, 26 of the shank. In a preferred embodiment, to accommodate some lateral rotational movement of the housing relative to the shank, there may be a space between the confronting side walls of the housing and the pair of side surfaces of the shank. Alternatively, the fit of the housing over the shank may be rather snug. The housing is seen to include a proximal face plate 48 which, in normal position, that is in assembly, is in abutting relation to the distally facing surface 50, 50' of the attachment means.

Within the housing there is a main chamber which, by reason of the stepped roof may be considered as having a distal cavity portion 52 extending proximally from the distal wall 40 and an intermediate cavity portion 54, between the face plate 48 and the distal cavity portion 52.

The housing is sized and configured to dwell on the shank with the roof of the housing being spaced from the upper surface of the shank, as is described more fully hereinafter.

Pivot means interconnect the housing and the shank, there being a recess 56 through the shank and in the side walls of the housing as at 57. The recess 56 in the shank is vertically elongated extending toward the lower surface of the shank. Within the pivot means there is provided a pin 58 in the aforementioned recesses 56 and 57. This is effective to permit hinged movement of the housing relative to the shank from the normal position of the face plate in abutting engagement with the distally facing surface 50, 50' of the attachment means as well as a range of vertical movement of the housing relative to the shank, which latter movement occurs because some movement vertically of the pin in the elongated recess 56 takes place upon the application of a vertical load.

In more detail, it is seen that the upper surface 20 of the shank includes an intermediate portion spaced from the housing roof 38 a predetermined distance, which is in the range of between about 0.4 and about 0.6 mm., for the purpose explained more fully above. The upper surface 20 of the distal portion 28 of the shank 18 is spaced beneath the housing roof 38 and this upper surface 20 is provided with a recess in it. This recess receives a resilient means 62 which is captivated in the recess 60 with a portion 64 at all times being adapted to be in engagement with the housing 32. This normally biases the housing 32 into the normal position, that is elevated and with the face plate in abutting relation with he attachment means, when the male/female attachment means connect the device to an abutment tooth. The resilient means it is seen are effective to permit vertical movement of the housing through the predetermined distance of between 0.4 and 0.6 mm., and, simultaneously, hinged movement of the housing, storing energy in the resilient means, which is effective to reboundingly restore the housing when masticating loads are cyclically relieved.

As shown in the drawings, the resilient means utilized comprise a member 62 with an upper surface 64 which is in engagement with the housing and a lower surface 66 which is in engagement with the shank in the recess 60. This member is of resilient, preferably rubbery material and is both vertically and distally, that is, swingably yieldable. As shown in the preferred embodiment, the resilient means 62 is weakened on its distal face by a cutout central portion 70 and, preferably, as seen in side elevation, when in assembly, it defines a Figure 8 configuration. Alternatively, other types of resilient members may be utilized within the spirit and scope of this invention.

To limit swinging movement, there is a surface 72 which is a stop means on the upper surface of the shank and adjacent the distal surface. This serves to limit pivotal movement of the housing relative to the shank. Further, to accommodate swinging movement, the distal surface 16 of the shank 18 adjacent the lower surface 22 is cut away as at 74 which permits tilting movement of the housing relative to the shank, that is sufficient clearance to accommodate the same. Also, the face plate 48 of the housing 32, adjacent the lower surface 22 of the shank 18, is cut away as at 76 which permits tilting movement of the face plate of the housing from the normal position in abutment with the attachment means at the surfaces 50, 50', when the same are in assembly.

In use, it is seen that the pivot pin 58 may be removed so that the shank may be removed from the housing and the resilient means 62 replaced from time to time to adjust the resiliency of the device.

As shown, the shank is integral with the male portion 78 of the attachment means; however, suitable fastening means may be provided to attach the shank to an existing male portion of a male/female attachment means.

While the instant invention has been shown and described in what is considered to be a practical and preferred embodiment, it is recognized that departures may be made within the spirit and scope of this invention, which is, therefore, not to be limited except as set forth in the claims which follow within the doctrine of equivalents.

What is claimed is:

1. A resilient denture connecting device having a proximal end and a distal end, a male-female attachment means to connect the device to an abutment tooth 12, said attachment means having a surface facing the gingival tissue 14 and a distally facing abutment surface 50, said attachment means including a distally extending rigid shank 18 adjacent the surface of the attachment means which faces the gingival tissue, said shank 18 having an upper surface 20 and a lower surface 22, said distal surface 16 and a pair of side surfaces 24–26 and including a distal portion 28 and an intermediate portion 30, a housing 32 having a roof 38 with an upper surface, a distal wall 40 with a distal surface, a pair of opposing side walls 42–44 and mouth in an open bottom 46, said housing being sized to receive the shank with the side walls of the housing 42–44 confronting the side surfaces 24–26 of the shank, said housing including a proximal face plate 48 in a normal position in abutting relation to the distally facing surface 50 of said attachment means, said housing having a distal cavity portion 52 extending proximately from the distal wall 40 and an intermediate cavity portion 54 between the face plate 48 and the distal cavity portion 52, pivot means interconnecting the side walls of the housing and the intermediate portion of the shank, said intermediate portion of the shank having a through recess 56 which is elongated toward the lower surface of the shank, and said pivot means including a pin 58 in the through recess 56 effective to permit hinged movement of the housing relative to the shank from said normal position of the face plate and vertical movement of the housing 32 relative to the shank upon movement of the pin vertically in the recess 56, said upper surface 20 of said shank including an intermediate portion spaced from the housing roof 38 a predetermined distance of between 0.4 and 0.6 millimeters, the upper surface 20 of said distal portion 28 of the shank 18 being spaced beneath the housing roof 38 and having a recess 60 in the upper surface 20 of the shank 18, resilient means 62 captivated in the recess 60 and with a portion 64 at all times in engagement with the housing 32 normally biasing the housing 32 into the normal position, when said male-female attachment means connect the device to an abutment tooth, said resilient means being effective to permit vertical movement of the housing simultaneously with hinged movement of said housing through said predetermined distance and said resilient means being effective to reboundingly restore the housing when masticating loads are cyclically relieved.

2. The device as set forth in claim 1 wherein said side surfaces 24–26 of said shank and side walls of the housing respectively are matingly spaced effective to permit some lateral rotational movement of the housing relative to the shank upon application of masticating loads.

3. The device as set forth in claim 1 wherein said resilient means comprises a member 62 having an upper surface 64 in engagement with the housing and a lower surface 66 in engagement with the shank 18 in the recess 60 and said resilient member 62 being distally and vertically yieldable.

4. The device as set forth in claim 3 wherein said resilient means 62 includes a weakened distally facing portion 68 and having a weakened central portion 70.

5. The device as set forth in claim 4 wherein said resilient means 62 as seen in assembly in side elevation has an outer surface defining a FIG. 8 configuration.

6. The device as set forth in claim 1 wherein said resilient means 62 comprises a plug of rubbery material.

7. The device as set forth in claim 1 wherein a portion 72 of the upper surface of said shank adjacent said distal surface comprises stop means to limit pivotal movement of the housing relative to the shank upon engagement with the roof of the distal cavity portion of the housing roof.

8. The device as set forth in claim 1 wherein said distal surface 16 of said shank 18 adjacent said lower surface 22 is cut away 74 to accommodate tilting movement of the housing relative to the shank.

9. The device as set forth in claim 1 wherein in assembly said face plate 48 of said housing 32 adjacent the lower surface 22 of the shank 18 is cut away 76 to permit tilting movement of the face plate of the housing relative to the attachment means.

10. The device as set forth in claim 1 wherein said pivot pin 58 is removable whereby the shank may be removed from the housing and said resilient means 62 replaced from time to time to adjust the resiliency of said device.

11. The device as set forth in claim 1 wherein said shank 18 is integral with the male portion 78 of said attachment means.

12. The device as set forth in claim 1 wherein said device includes means to attach said shank to said attachment means.

* * * * *